United States Patent [19]

Morita et al.

[11] Patent Number: 5,183,662
[45] Date of Patent: Feb. 2, 1993

[54] CONTROLLED DRUG RELEASE COMPOSITION

[75] Inventors: Yasushi Morita, Osaka; Akira Ohtori, Fukuoka; Masako Andoh, Hyogo, all of Japan

[73] Assignee: Senju Pharmaceutical Co., Ltd., Osaka, Japan

[21] Appl. No.: 750,482

[22] Filed: Aug. 27, 1991

[30] Foreign Application Priority Data

Aug. 30, 1990 [JP] Japan ................................. 2-229887

[51] Int. Cl.$^5$ ........................ A61K 9/14; A61K 9/70; A61K 31/56
[52] U.S. Cl. .................................... 424/426; 424/422; 424/425; 424/484; 424/486; 514/772.3
[58] Field of Search ............... 424/422, 425, 426, 484, 424/486; 514/169, 772.3

[56] References Cited

U.S. PATENT DOCUMENTS 4,432,964  2/1984  Shell et al. ........................... 424/427

FOREIGN PATENT DOCUMENTS 1391554  8/1972  United Kingdom ................. 424/486
2091554  8/1988  United Kingdom ................. 424/486

Primary Examiner—Thurman K. Page
Assistant Examiner—Carlos Azpuru
Attorney, Agent, or Firm—Wenderoth, Lind & Ponack

[57] ABSTRACT

The present invention is concerned with a controlled drug release composition comprising a poorly soluble drug, a water-soluble macromolecular compound and biodegradable macromolecular compound, which composition can be freely tailored to the required solubility and release pattern of the poorly soluble drug through adjustment of the ratio of said ingredients.

3 Claims, 4 Drawing Sheets

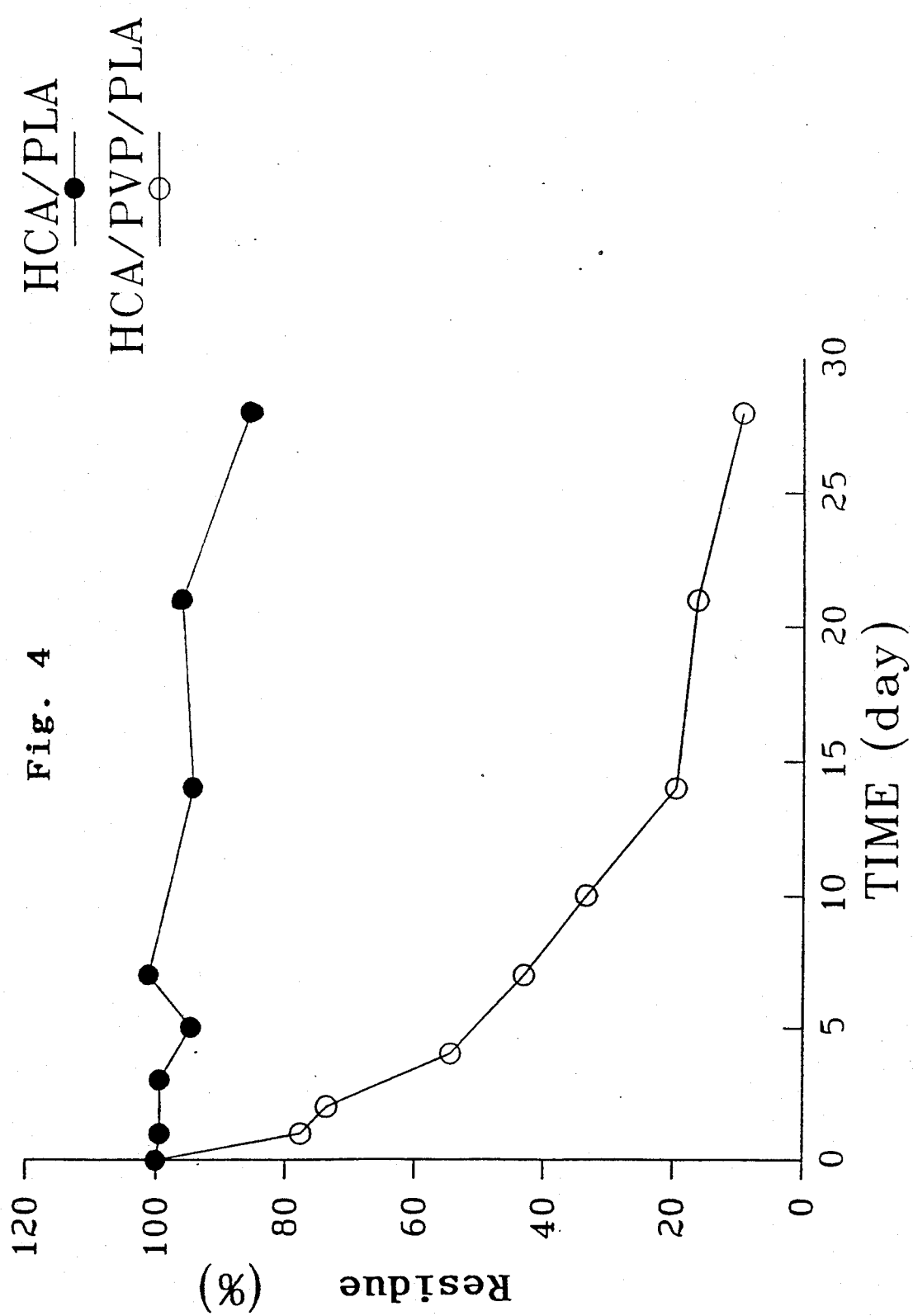

CONTROLLED DRUG RELEASE COMPOSITION

BACKGROUND OF THE INVENTION

1. Field of the Invention

The present invention relates to a composition comprising a poorly soluble drug, a water-soluble macromolecular compound and a biodegradable macromolecular compound. More particularly, the invention relates to a composition comprising a poorly soluble drug, a water-soluble macromolecular compound and a biodegradable macromolecular compound and as such insuring increased solubility and well controlled release of said poorly soluble drug.

2. Description of Prior Art

It is known that in the administration of a poorly soluble drug, the rate of dissolution of the drug is determinant of the rate of absorption of the drug in many instances and that the solubility of the drug has a profound influence on the bioavailability of the drug. A diversity of methods have been proposed for enhancing the dissolution rate of poorly soluble drugs. There are reports, for instance, on the preparation of a coprecipitate between a poorly soluble drug and a highly water-soluble macromolecular substance such as polyvinylpyrrolidone and the use of the coprecipitate as an oral medicine [Shotaro Sakurai et al.: The Archives of Practical Pharmacy, 47, 191–196 (1987) or a suppository (Yoshiko Hamamoto et al.: The Archives of Practical Pharmacy, 49, 209–214 (1989)].

It is true that the dissolution of the poorly soluble drug from such a coprecipitate prepared by these prior art technologies is rapid indeed but the rate of release of the drug can hardly be controlled. Therefore, there are defects that it is impossible to supply the recipient body with a sufficient amount of the drug to maintain a therapeutically effective concentration and thus its sufficient efficacy cannot be expected. Moreover, the risk has been pointed out that the rate of release may sometimes be so rapid that more than the necessary amount of the drug is released at a time to cause adverse reactions.

Under the circumstances the development of a therapeutic system (composition) insuring enhanced solubility and controlled release of a poorly soluble drug has been keenly demanded in the pharmaceutical field.

Accordingly, in view of these circumstances, the inventors of the present invention explored this field of technology with due diligence for establishing a composition which would be free from the above-mentioned disadvantages and capable of insuring enhanced solubility and well controlled release of a poorly soluble drug and discovered that these requirements can be met by providing a composition comprising a poorly soluble drug, a water-soluble macromolecular compound and a biodegradable macromolecular compound. This finding was followed by further research, which has culminated in the present invention.

SUMMARY OF THE INVENTION

The present invention is, therefore, concerned with a controlled drug release composition comprising a poorly soluble drug, a water-soluble macromolecular compound and biodegradable macromolecular compound, which composition can be freely tailored to the required solubility and release pattern of the poorly soluble drug through adjustment of the ratio of said ingredients.

DETAILED DESCRIPTION OF THE INVENTION

The poorly soluble drug which can be used in the composition of the invention includes, inter alia, various steroidal compounds such as hydrocortisone, hydrocortisone acetate, dexamethasone, fluorometholone and so on.

The water-soluble macromolecular compound which is used in the composition of the invention may be any appropriate high molecular weight compound that is physiologically harmless. Thus, for example, polyvinylpyrrolidone, polyethylene glycol, hydroxypropylcellulose, etc. can be mentioned. The average molecular weight of the water-soluble macromolecular compound to be used for the invention is generally in the range of about 5,000 to about 5,000,000, preferably from about 10,000 to about 1,000,000 according to the intended release pattern of the poorly soluble compound and so on. These compounds can be employed singly or in a suitable combination according to the intended application.

The biodegradable macromolecular compound which is used in the composition of the invention is a high molecular weight compound which is physiologically acceptable and decomposes in the body and is absorbed. Thus, for example, polylactic acid and polyglycolic acid, inclusive of the corresponding copolymers, can be mentioned. The average molecular weight of the biodegradable macromolecular compound to be used for the invention is generally in the range of about 200 to about 100,000, preferably from about 1,000 to about 10,000, according to the intended release pattern of the poorly soluble compound and so on.

The composition of the present invention can be manufactured by the solid dispersion method (W. L. Chiou et al., J. Pharm. Sci., 60, 1281 (1971)) which is commonly employed. However, it is preferable to employ the solvent evaporation method which comprises dissolving uniformly a poorly soluble drug, a water-soluble macromolecular compound and a biodegradable macromolecular compound in an organic solvent and removing the solvent by evaporation. The organic solvent to be used in such solvent evaporation method may be virtually any solvent that is capable of dissolving the poorly soluble drug, water-soluble macromolecular compound and biodegradable macromolecular compound and, at the same time, can be easily distilled off. Particularly preferred examples are ethanol, acetonitrile, acetone and chloroform. These solvents can be used either singly or in an appropriate combination according to the intended application.

In preparing the composition of the invention, the formulating ratio of the poorly soluble drugs, water-soluble macromolecular compound and biodegradable macromolecular, compound can be freely selected according to the desired rate of release of the poorly soluble drug. While this formulating ratio should vary with different species of compounds used and the contemplated method of administration, it is generally recommended to use about 1–10 weight parts of the water-soluble macromolecular compound and about 1 to 10 weight parts of the biodegradable macromolecular compound per weight part of the poorly soluble drug. The more preferred proportions are about 3 to 5 weight parts of the water-soluble macromolecular compound and about 1 to 3 weight parts of the biodegradable macromolecular compound per weight part of the poorly soluble drug.

The composition of the present invention, which is thus available upon removal of the organic solvent, can be used as it is. However, according to the intended application such as the indicated site of action of the drug, the composition can be further processed, with great ease, into such dosage forms as the disk, rod, film, sheet, microcapsule and so on. By way of example, such a dosage form can be easily prepared by dissolving the poorly soluble drug, water-soluble macromolecular compound and biodegradable macromolecular compound in an organic solvent, removing the solvent by evaporation, drying the residue under reduced pressure, pulverizing the dry residue and molding the resulting powder into a disk, rod or the like in the conventional manner. In the case of a rod, the above pulverized residue can also be molded by the pressure-heat melting method. A film or sheet can be manufactured by dissolving the same in an organic solvent and casting the solution. If desired, a film or a microcapsule can be manufactured by the conventional technology in the course of removal of the solvent. For example, microcapsules can be manufactured by the so-called in-liquid drying method which comprises dispersing an organic solvent solution of the three ingredients in cottonseed oil, castor oil or the like and removing the solvent by distillation.

The composition of the invention can thus be used in a variety of dosage forms and such preparations can be selectively applied to indicated sites, such as the skin, eye, ear, nose, oral cavity or vagina, according to diseases, or orally for the treatment of systemic diseases.

Unless contrary to the objects of the invention, the composition of the present invention can be formulated with excipients which are commonly incorporated in various pharmaceutical preparations.

Compared with the conventional composition comprising a poorly soluble drug and a water-soluble macromolecular compound, the composition of the present invention not only insures a remarkably increased solubility of the drug but also a tailored release of the drug, besides being moldable into a variety of dosage forms, thus being an excellent composition.

EXAMPLE

The following examples are further illustrative of the present invention.

EXAMPLE 1

Solubility Testing of Hydrocortisone Acetate Compositions

Hydrocortisone acetate (HCA), polyvinylpyrrolidone (PVP) [average molecular weight: 40,000] and polylactic acid (PLA) [average molecular weight: 6,000] were mixed according to the formulas shown below and each mixture was dissolved in 50 ml of acetonitrile. The acetonitrile was gradually distilled off under reduced pressure at about 60° C. and the residue was dried in vacuo at room temperature for 16 hours to give a hydrocortisone acetate composition.

| No. | Hydrocortisone acetate | Polyvinyl-pyrrolidone | Polylactic acid |
|---|---|---|---|
| 1 | 0.1 g | 0.1 g | — |
| 2 | 0.1 g | 0.5 g | — |
| 3 | 0.1 g | 1.0 g | — |
| 4 | 0.1 g | — | 0.1 g |
| 5 | 0.1 g | 0.1 g | 0.1 g |
| 6 | 0.1 g | 0.1 g | 0.3 g |
| 7 | 0.1 g | 0.3 g | 0.1 g |
| 8 | 0.1 g | 0.5 g | 0.3 g |

Each of the hydrocortisone acetate compositions thus prepared was added to 50 ml of 1/150M phosphate buffer (pH 7.2) to provide to a test sample containing about 5 mg of hydrocortisone acetate and the solubility of hydrocortisone acetate at 37° C. was determined.

As shown in FIG. 1, the HCA-polyvinylpyrrolidone compositions gave solubility values about two- to three-fold the solubility of the active drug used alone. On the other hand, as shown in FIG. 2, the compositions of the invention, which contained both polyvinylpyrrolidone and polylactic acid, gave remarkably higher solubilities, e.g., in the case of composition No. 8 more than about six-fold as high after 60 minutes.

EXAMPLE 2

Solubility Testing of Hydrocortisone, Dexamethasone and Fluorometholone Compositions In 50 ml of ethanol-acetonitrile (4/1) were dissolved 0.1 g of hydrocortisone (HC), dexamethasone (DM) or fluorometholone (FLU), 0.5 g of polyvinylpyrrolidone [average molecular weight: 40,000] and 0.3 g of polylactic acid [average molecular weight: 2,000] and the solution was processed into a composition in the same manner as Example 1.

Each of the three steroid compositions thus prepared was added to 50 ml of 1/150M phosphate buffer (pH 7.2) to provide a sample containing about 5 ml of the steroid and the solubility of the drug at 37° C. was evaluated.

The results are shown in FIG. 3. After 60 minutes, the solubility of the steroid drug was increased by 1.4 fold in the case of the hydrocortisone composition, 1.7 fold in in the case of the dexamethasone composition and 5.2-fold in the case of the fluorometholone composition.

EXAMPLE 3

Solubility Testing of Hydrocortisone Acetate Compositions

In 50 ml of ethanol-acetonitrile (¼) were dissolved 0.1 g of hydrocortisone acetate, 0.5 g of polyvinylpyrrolidone [average molecular weight: 40,000], polyethylene glycol [average molecular weight: 4,000] or hydroxypropylcellulose [average molecular weight: 60,000], and 0.3 g of polylactic acid [average molecular weight: 4,000] and the solubility of the steroid was determined as in Example 2.

The results were similar to those obtained in Example 2.

EXAMPLE 4

Solubility Testing of Hydrocortisone, Dexamethasone and Fluorometholone Compositions The same amounts of the same ingredients as used in Example 2 were respectively dissolved in chloroform or acetone-acetonitrile (¼) and the solutions were processed into compositions as in Example 1. These compositions gave solubility results similar to those described above.

EXAMPLE 5

Release Testing of Hydrocortisone Acetate

The hydrocortisone acetate composition (No. 8) prepared in Example 1 was filled into a Teflon tube having an inside diameter of 0.8 mm and pushed with a stainless steel push-rod from either end at about 80° C. to give a rod having a diameter of 0.8 mm and a length of 5 mm.

This rod was immersed and shaken in 100 ml of 1/150M phosphate buffer (pH 7.2) at 37° C. to evaluate the time course of release.

As shown in FIG. 4, the release followed the 0-order pattern. It was found that the release of the drug from the rod molded from a binary mixture of the hydrocortisone acetate and polylactic acid [average molecular weight: 2,000] in the same manner as Example 5 was much retarded as compared with the release from the rod molded from the composition (No. 8).

EXAMPLE 6

Microcapsule

The same amounts of the same ingredients as used in Example 2 were respectively dissolved in 30 ml of ethanolacetonitrile (2:1) and each solution was added dropwise to 100 ml of cottonseed oil containing 2 g of soybean lecithin under constant stirring at 1,500 rpm. The mixture was further stirred at about 65° C. for 6 hours. The mixture was then centrifuged at 5,000 rpm for 10 minutes, washed with hexane and dried in vacuo at room temperature for 16 hours to give microcapsules sized about 1 μm.

EXAMPLE 7

Film

The same amounts of the same ingredients as used in Example 2 were respectively dissolved in 50 ml of acetone-acetonitrile (9:1) and each solution was cast in a Teflon vessel and dried at room temperature to provide a sheet.

This sheet was then calendered to give a film having a thickness of about 600 μm.

BRIEF DESCRIPTION OF THE DRAWINGS

FIG. 4 shows the pattern of release from a hydrocortisone acetate-polyvinylpyrrolidone-polylactic acid rod, where the ordinate represents the % residue of hydrocortisone acetate in the rod and the abscissa represents time (days).

Figure 1:
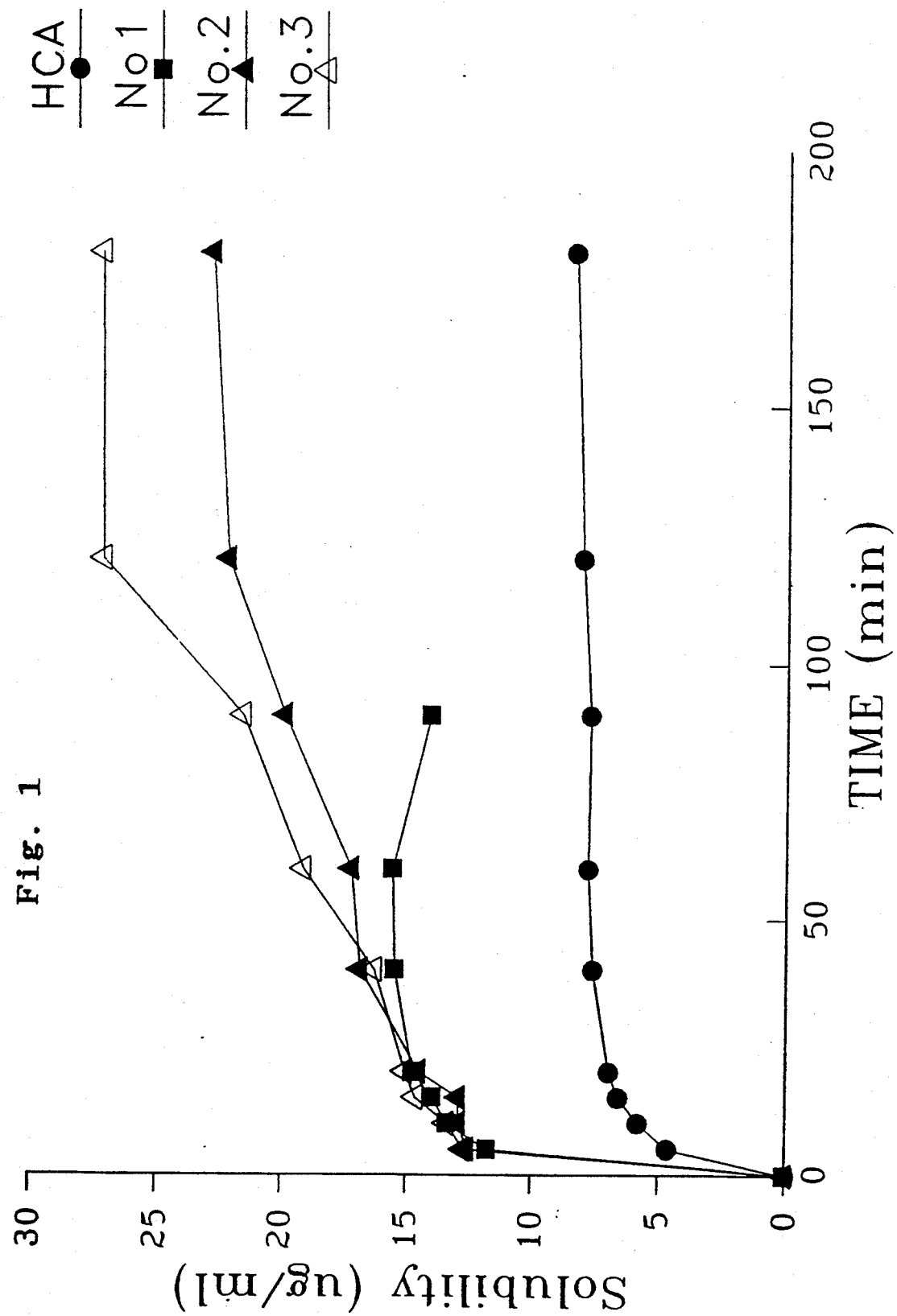
FIG. 1 is a diagram showing the solubility of hydrocortisone acetate-polyvinylpyrrolidone compositions, where the ordinate represents solubility and the abscissa represents time (minutes).
Figure 2:
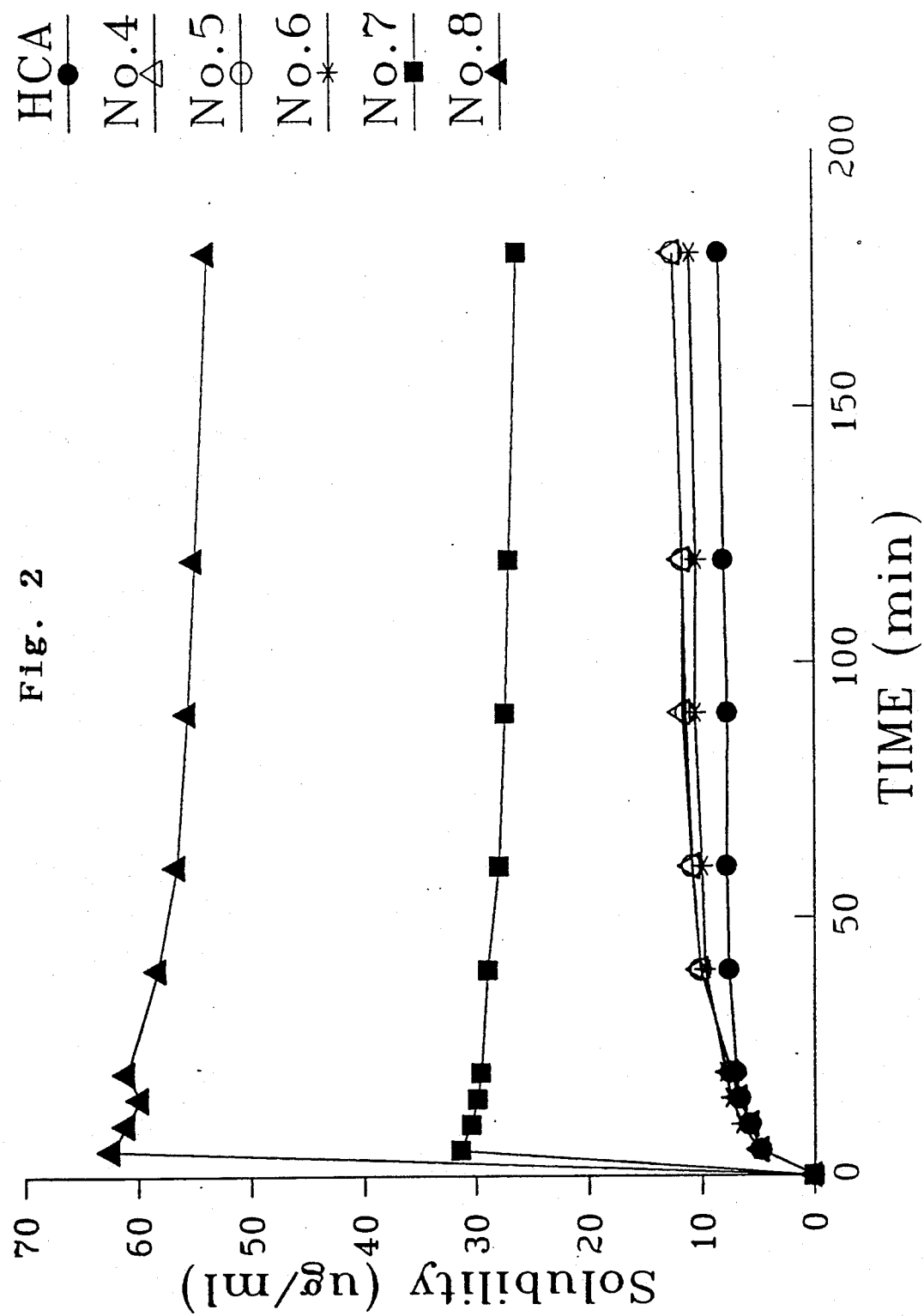
FIG. 2 is a diagram showing the solubilities of hydrocortison acetate-polyvinylpyrrolidone-polylactic acid compositions, where the ordinate represents solubility and the abscissa represents time (minutes).
Figure 3:
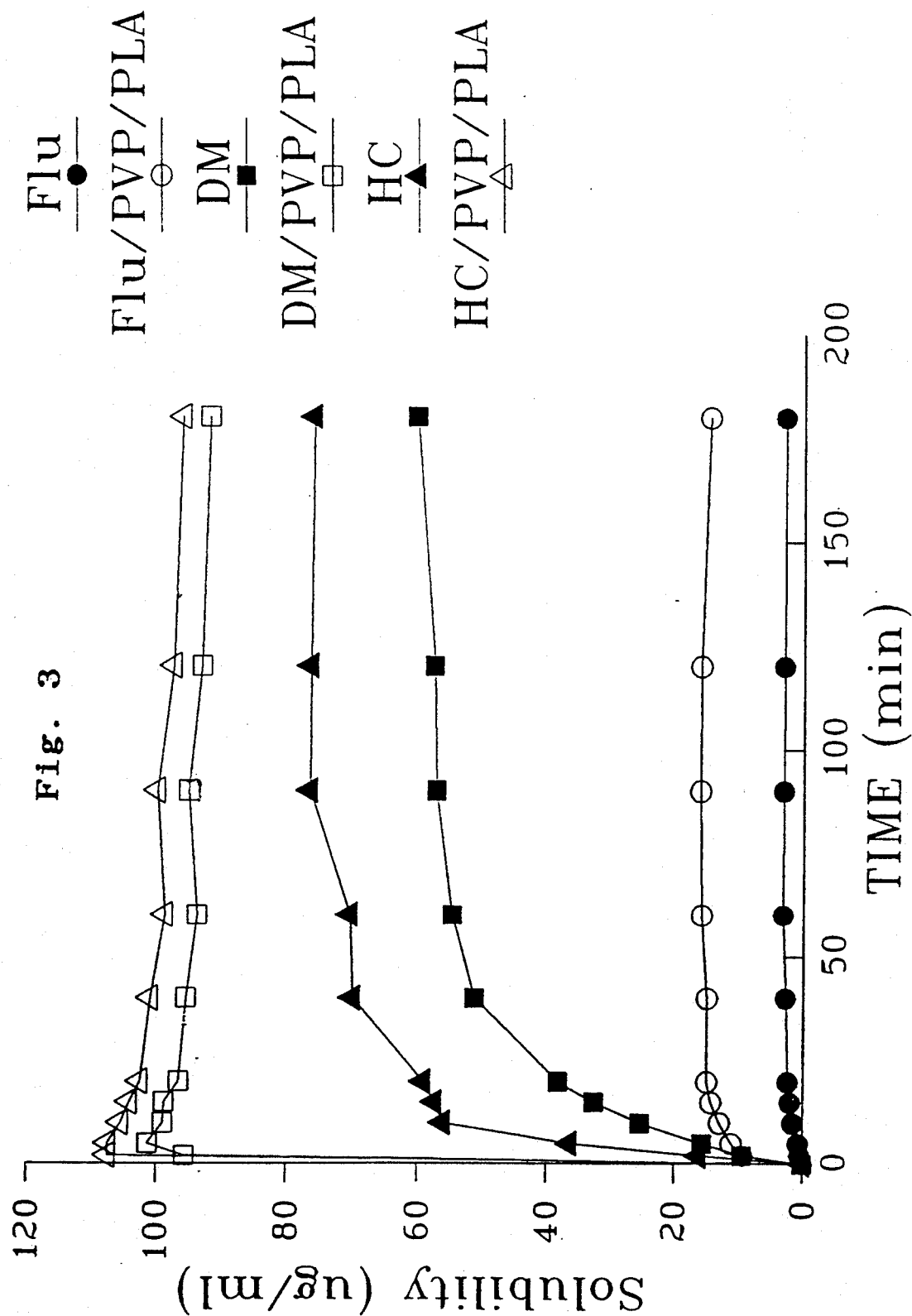
FIG. 3 is a diagram showing the solubility of a hydrocortisone/dexamethasone/ or fluorometholone-polyvinylpyrrolidone-polylactic acid composition, where the ordinate represents solubility and the abscissa represents time (minutes).

What is claimed is:

1. A controlled drug release composition which comprises at least one poorly soluble steroidal drug; at least one water-soluble macromolecular compound selected from the group consisting of polyvinylpyrrolidone, polyethylene glycol and hydroxypropylcellulose in a proportion of 3 to 5 weight parts per weight part of the poorly soluble drug; and at least one biodegradable macromolecular compound selected from the group consisting of polylactic acid, polyglycolic acid and the corresponding copolymers thereof in a proportion of 1 to 3 parts per weight part of the poorly soluble drug.

2. A controlled drug release composition according to claim 1 in the dosage form of a rod, sheet, film, disk or microcapsule.

3. A controlled drug release composition in dosage form of a rod or sheet which comprises at least one poorly soluble steroidal drug; at least one water-soluble macromolecular compound selected from the group consisting of polyvinylpyrrolidone, polyethylene glycol and hydroxypropylcellulose in a proportion of 3 to 5 weight parts per weight part of the poorly soluble drug; and at least one biodegradable macromolecular compound selected from the group consisting of polylactic acid, polyglycolic acid and the corresponding copolymers thereof in a proportion of 1 to 3 parts per weight part of the poorly soluble drug.

* * * * *